(12) United States Patent
Baydoun et al.

(10) Patent No.: US 9,173,888 B1
(45) Date of Patent: Nov. 3, 2015

(54) TREATMENT AND INHIBITION OF PROTOZOAL DISEASES WITH NANDROLONE AND ITS DERIVATIVES

(71) Applicants: Elias Baydoun, Beirut (LB); Muhammad Iqbal Choudhary, Karachi (PK); Atia-tul-Wahab, Karachi (PK); Colin Smith, Beirut (LB); Martin Karam, Beirut (LB); Dina Farran, Beirut (LB); Mahwish Shafi Ahmed Khan, Karachi (PK); Malik Shoaib Ahmad, Karachi (PK)

(72) Inventors: Elias Baydoun, Beirut (LB); Muhammad Iqbal Choudhary, Karachi (PK); Atia-tul-Wahab, Karachi (PK); Colin Smith, Beirut (LB); Martin Karam, Beirut (LB); Dina Farran, Beirut (LB); Mahwish Shafi Ahmed Khan, Karachi (PK); Malik Shoaib Ahmad, Karachi (PK)

(*) Notice: Subject to any disclaimer, the term of this patent is extended or adjusted under 35 U.S.C. 154(b) by 0 days.

(21) Appl. No.: 14/289,395

(22) Filed: May 28, 2014

(51) Int. Cl.
  *A61K 31/56* (2006.01)
  *A61K 31/565* (2006.01)
  *C12Q 1/18* (2006.01)
  *A61K 31/566* (2006.01)

(52) U.S. Cl.
  CPC .............. *A61K 31/565* (2013.01); *A61K 31/566* (2013.01); *C12Q 1/18* (2013.01)

(58) Field of Classification Search
  None
  See application file for complete search history.

(56) References Cited

PUBLICATIONS

Ciaramella et al., "Canine Leishmaniasis: Therapeutic Aspects," vol. 25, No. 5 May 2003.*

* cited by examiner

*Primary Examiner* — Craig Ricci
*Assistant Examiner* — Jared D Barsky
(74) *Attorney, Agent, or Firm* — Sarfaraz K. Niazi

(57) ABSTRACT

This invention provides new therapeutic potential of nandrolone or a derivative thereof, against protozoal diseases. More specifically, nandrolone or a derivative thereof exhibits anti-protozoal activity against *Leishmania major*. Anti-protozoal potential of nandrolone derivatives, such as compounds 1-8, can contribute in the development of effective therapies against protozoal diseases, such as leishmaniasis, trypanosomiasis, malaria, toxoplasmosis, babeosis, amoebic dysentery and lambliasis. Another aspect of the invention is a method of testing derivatives of nandrolone for anti-protozoal activity comprising growing *Leishmania* in the presence of the test derivative and determining the $IC_{50}$ value.

1 Claim, 2 Drawing Sheets

TREATMENT AND INHIBITION OF PROTOZOAL DISEASES WITH NANDROLONE AND ITS DERIVATIVES

BACKGROUND OF THE INVENTION

Leishmiansis remains one of the major health problems in developing countries. It is a vector born disease affecting 88 countries: 72 of which are developing and 13 are the least developed. A protozoan parasite belongs to genus *Leishmania* is the major cause of leishmaniasis (Desjeux, P., (2004), Leishmaniasis: current situation and new perspectives, Comparative Immunology, Microbiology & Infectious Diseases, 27, 305-318.)

There are three major forms of leishmaniasis, which include visceral leishmaniasis, mucocutaneous leishmaniasis and cutaneous leishmaniasis. Visceral leishmaniasis (kala azar or black fever) is the most severe form of leishmaniasis and becomes fatal when it remains untreated. In mucocutaneous leishmaniasis, lesions lead to complete or partial destruction of mucous membranes of the mouth and throat cavity, as well as the nose and other surrounding tissues. Cutaneous leishmaniasis is the most common form of leishmaniasis and is transmitted through the bite of the female sand fly (Phlebotomine). The *Leishmania* parasite multiplies in the gut of the sand fly and becomes infective in 8-20 days. Sand flies act as a vector where it transmits the disease from one affected person to others.

Nandrolone is an anabolic androgenic steroid known as a performance drug. It is also called a 19-noretestosterone, because of its similar structure to testosterone. The only difference is a missing methyl group at C-10. Nandrolone is commercially marketed as its decanoate (deca-durabolin) and phenylpropionate ester (durabolin). The interesting chemistry and diverse biological properties make nandrolone an important class of bioactive compounds.

In an effort to discover new leishmanicidal agents, we synthesized a series of nandrolone derivatives through biotransformation. These derivatives were evaluated for their potential as anti-protozoal agents. The anti-protozoal properties of nandrolone and its derivatives provide an unmet medical need in countries where patients suffer from protozoal infections.

SUMMARY OF THE INVENTION

The present invention involves a method of treating a protozoal disease, such as leishmaniasis, trypanosomiasis, malaria, toxoplasmosis, babeosis, amoebic dysentery or lambliasis with an effective amount of nandrolone or a derivative thereof. The nandrolone derivatives may be synthesized through biotransformation using a microorganism, such as *Cunninghamella echinulata* or *Cunninghamella blakesleeana*.

Another aspect of the invention is inhibiting a protozoal infection of a patient in need thereof comprising administering an effective amount of nandrolone or a derivative thereof.

Another aspect of the invention is the testing of a nandrolone derivative compound for anti-protozoal activity comprising an anti-leishmanial assay wherein the assay comprises culturing the *Leishmania* promastigote in the presence of the test compound and determining the $IC_{50}$ value. An $IC_{50}$ value between 0 and 35 indicates an effective compound.

DETAILED DESCRIPTION OF THE INVENTION

Figure 1:
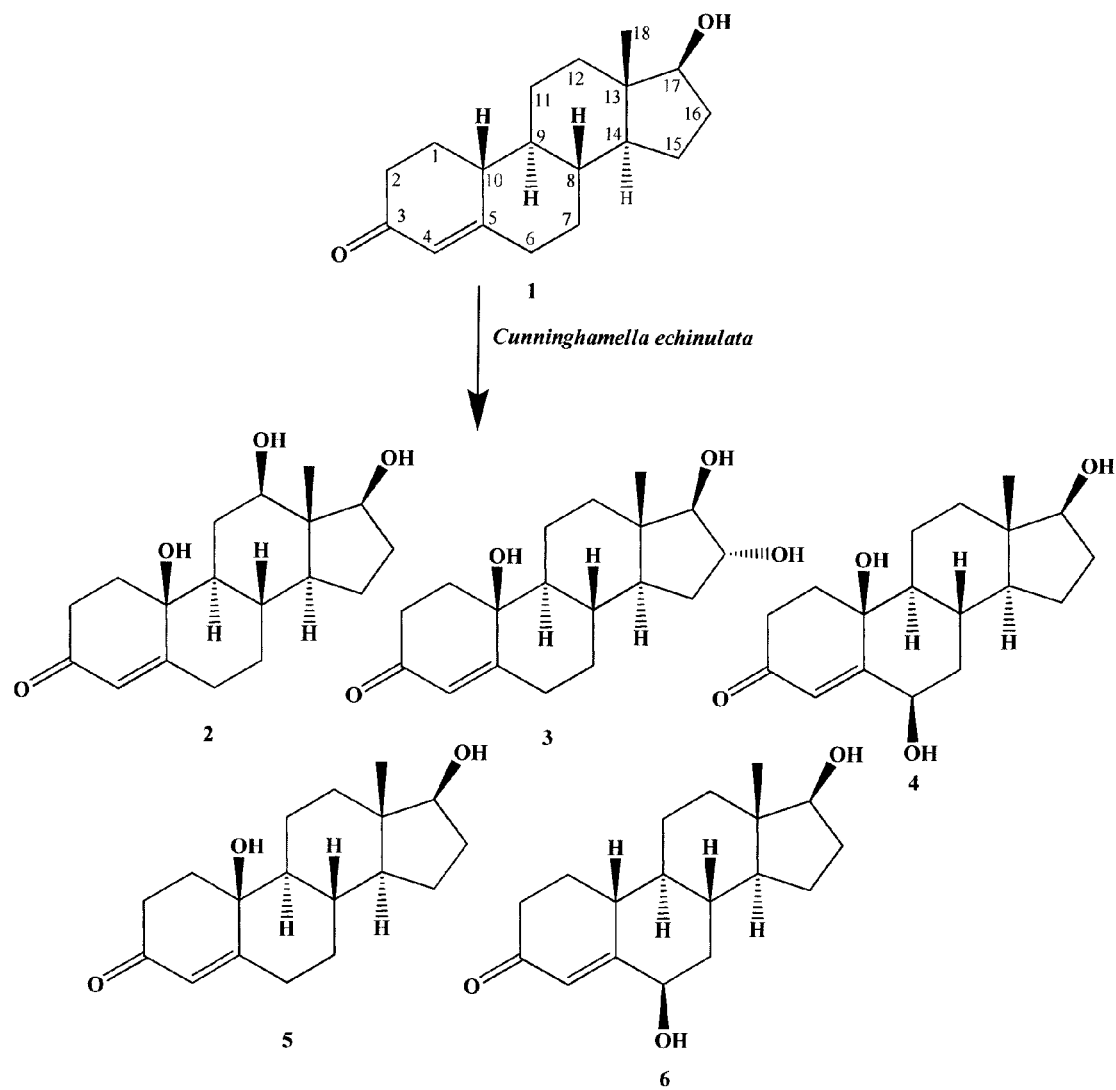
FIG. 1 depicts the structures of nandrolone (1) and its biotransformed derivatives, 10β,12β,17β-trihydroxy-19-nor-4-androsten-3-one (2), 10β,16α,17β-trihydroxy-19-nor-4-androsten-3-one (3), 6β,10β,17β-trihydroxy-19-nor-4-androsten-3-one (4), along with two known metabolites, 10β,17β-dihydroxy-19-nor-4-androsten-3-one (5), and 6β,17β-dihydroxy-19-nor-4-androsten-3-one (6) by using *Cunninghamella echinulata*.
Figure 2:
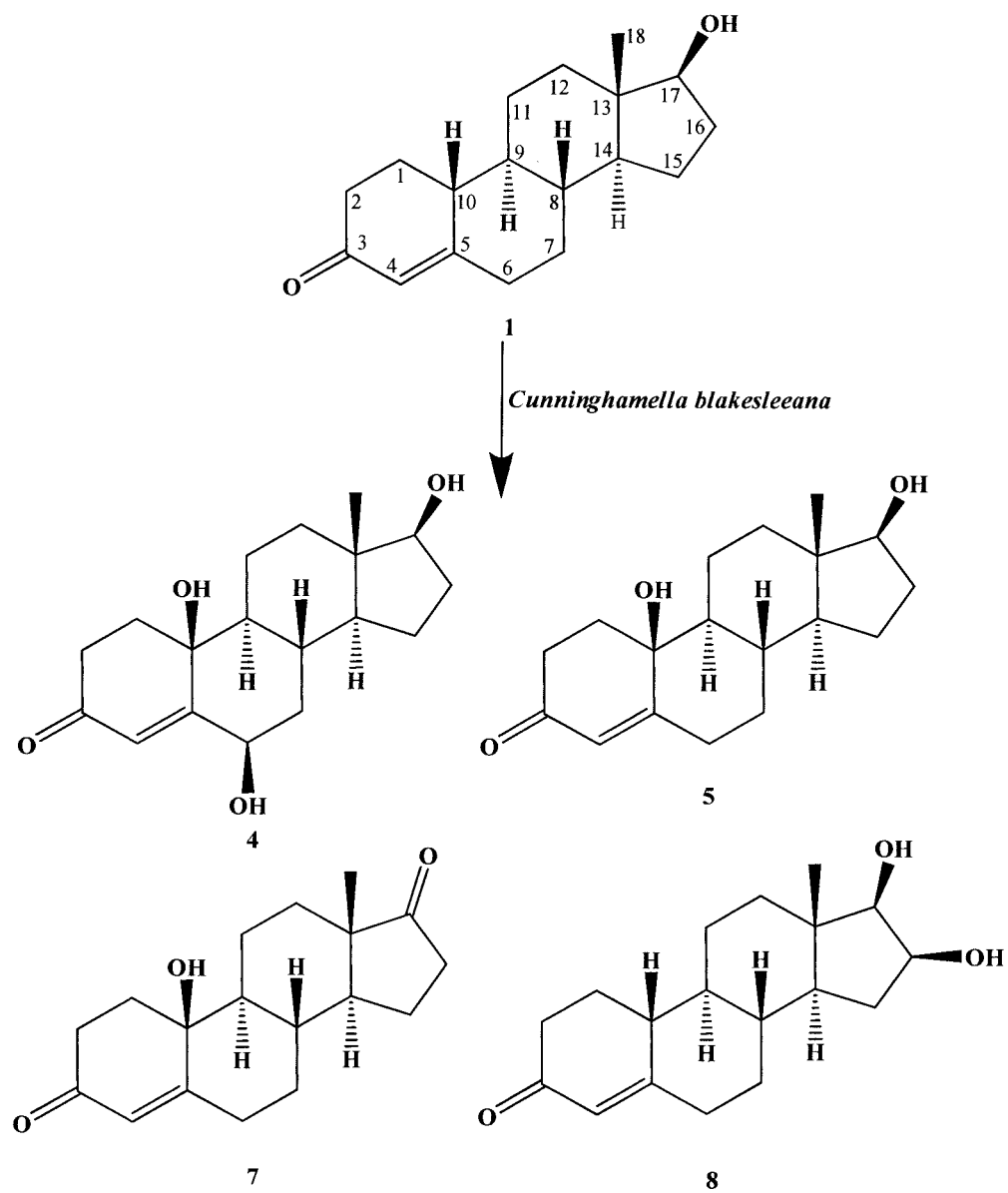
FIG. 2 depicts the structures of nandrolone (1) and its biotransformed derivatives, 6β, 10β,17β-trihydroxy-19-nor-4-androsten-3-one (4), 10β,17β-dihydroxy-19-nor-4-androsten-3-one (5), 10β-hydroxy-19-nor-4-androsten-3,17-dione (7) and 16β,17β-dihydroxy-19-nor-4-androsten-3-one (8) with *Cunninghamella blakesleeana*.

General Experimental Conditions of Biotransformation of Nandrolone:

Nandrolone (1) was obtained from Sigma-Aldrich. Sabouraud dextrose agar used for culture growth was procured from Merck. Precoated TLC plates were used for thin layer chromatography (Merck, $PF_{254}$, 20×20, 0.25 mm, Germany). Column chromatography was done with flash silica. Compounds were purified on recycling preparative HPLC-LC-908 (Japan), equipped with JAIGEL-ODS-L-80 (L=250 mm, I.D.=20 mm. Optical rotations were recorded on JASCO P-2000 polarimeter (Japan). Evolution 300 UV-visible spectrophotometer (UK) was used for recording UV Spectrum. Infrared (IR) spectrum was measured on Vector 22 IR spectrophotometer (Bruker, France). $^1$H- and $^{13}$C-NMR experiments were recorded in $CD_3OD$, $CDCl_3$ and DMSO on Bruker Avance-NMR (300 MHz 500 MHz and 600 MHz). Electron impact mass spectra (EI-MS) were recorded on Jeol JMS-600H mass spectrometer. Solvents and reagents were of analytical grades.

Microorganisms:

Fungus culture were purchased from American Type Culture Collection (ATCC). *Cunninghamella echinulata* (ATCC 9244) and *Cunninghamella blakesleeana* (ATCC 8688A) were cultured on sabouraud dextrose agar (SDA) slant and maintained at 4° C.

Media Preparation:

Culture media for *Cunninghamella echinulata* (ATCC 9244) and *Cunninghamella blakesleeana* (ATCC 8688A) were prepared by mixing the giving ingredients in one liter of distilled water; glucose (10 g), $KH_2PO_4$ (5 g) peptone (5 g), yeast extract (5 g), NaCl (5 g) and glycerol (10 mL).

General Fermentation and Extraction Conditions:

Five liter of the medium was prepared by mixing of aforementioned chemicals and distributed equally in fifty 250 mL Erlenmeyer flasks (100 mL each). The media containing flasks were autoclaved at 121° C. The fungal spores were distributed to 3-4 seed flasks and incubated on shaker (121 rpm) at 26±2° C. till appropriate growth. The spores were then transferred to the remaining flasks and placed on shaker (121 rpm at 26±2° C.). Nandrolone (1) (1 g) was dissolved in 50 mL of methanol, transferred to the flasks containing four day old culture of *Cunninghamella echinulata* and *Cunninghamella blakesleeana*. The fermentation experiment was continued for 12 days on shaker. On completion of fermentation, the reaction was inhibited by adding dichloromethane and fungal mass was separated by filtration. The extraction of filtrate was done with DCM (4 L×3), extract was dried with anhydrous sodium sulfate and evaporated on rotary evaporator to obtain a brown thick material.

Fermentation of Nandrolone (1) with *Cunninghamella echinulata*:

One gram of nandrolone (1) was subjected to fermentation for 12 days with *Cunninghamella echinulata* on a rotatory shaker (121 rpm) at 26+2° C. The filtration, extraction and evaporation resulted brown gum of 1.5 g which was fractionated with silica gel column chromatography. The mobile phase was comprised of 10% gradient hexanes enriched with ethyl acetate. Four main fractions (NANO 1-4) were obtained after compilation of different fractions. Compound 5 (2.5 mg, $R_T$=22 min) and 6 (5 mg, $R_T$=31 min.) were isolated from fraction NANO-1 with reverse phase recycling HPLC (Methanol: water 60:40). Similarly, fraction NANO-2 was subjected to recycling HPLC (chloroform: isopropanol 94:06), which yielded metabolite 4 (6 mg, $R_T$=184 min). Fraction NANO-3 yielded metabolite 2 (2 mg) on elution of silica gel column (10% gradient hexanes and ethyl acetate=15:85), and compound 3 (15 mg, $R_T$=204 min) was isolated from fraction NANO-4 through purification with reverse phase recycling HPLC (Methanol: water 70:30).

Fermentation of nandrolone with *Cunninghamella blakesleeana*:

Fermentation of nandrolone (1) with *C. blakesleeana* yielded four metabolites (4, 5, 7 and 8). Incubation, filtration, and extraction procedure was similar as mentioned before. Silica gel column chromatography yielded four main fractions (NACB 1-4). Compound 4 (5 mg) was purified from fraction NABC-1 with recycling HPLC (chloroform: isopropanol, 94:06 $R_T$=184 min), whereas compound 5 was isolated from NABC-2 on elution with reverse phase recycling HPLC (MeOH: $H_2O$, 60:40, $R_T$=42 min.). The metabolites 7 and 8 were purified with silica gel column chromatography by using hexanes and ethyl acetate as solvents (70:30).

10β,12β,17β-Trihydroxy-19-nor-4-androsten-3-one (2): White solid; log ε=1.97; $[α]_D^{25}$=−126.2 (c 0.018, MeOH); IR (KBr); $υ_{max}$ 3419 (O—H stretching), 1663 (C=O stretching); HREI-MS m/z 306.1842 ($M^+$, $[C_{18}H_{26}O_4]^+$, calc. 306.1831); EI-MS: m/z 306.2 [$M^+$](25), 288.2 (16), 278.2 (49), 190.2 (39); $^1$H-NMR ($CD_3OD$, 300 MHz): Table 2; $^{13}$C-NMR ($CD_3OD$, 125 MHz): Table 3.

10β,16α,17β-Trihydroxy-19-nor-4-androsten-3-one (3): White solid; log ε=3.4; 2.8 $[α]_D^{25}$=62.5 (c 0.01, MeOH); IR ($CHCl_3$); $υ_{max}$ 3388 (O—H stretching), 1664 (C=O stretching); HREI-MS m/z 306.1840 ($M^+$, $[C_{18}H_{26}O_4]^+$, calc. 306.1831); EI-MS: m/z 306.2 [$M^+$](40), 288.3 (30), 278.3 (89), 264.2 (21), 213.2 (66); $^1$H-NMR ($CD_3OD$, 300 MHz): Table 2; $^{13}$C-NMR ($CD_3OD$, 150 MHz): Table 3.

6β,10β,17β-Trihydroxy-19-nor-4-androsten-3-one (4): White solid; log ε=3.4; $[α]_D^{25}$=−257.5 (c 0.02, MeOH); IR ($CHCl_3$); $υ_{max}$ 3392 (O—H stretching), 1669 (C=O stretching); HREI-MS m/z 306.1819 ($M^+$, $[C_{18}H_{26}O_4]^+$, calc. 306.1831); EI-MS: m/z 306.2 [$M^+$] (100), 259.2 (10), 138.1 (18.8), 133.1 (16), 91.1 (14.4); $^1$H-NMR ($CD_3OD$, 300 MHz): Table 2; $^{13}$C-NMR ($CD_3OD$, 125 MHz): Table 3.

10β,17β-Dihydroxy-19-nor-4-androsten-3-one (5): White solid; log E=3.34 $[α]_D^{25}$=274.2 (c 0.07, MeOH); IR ($CHCl_3$); $υ_{max}$ 3406 (O—H stretching), 1656 (C=O stretching); HREI-MS m/z 290.1900 ($M^+$, $[C_{18}H_{26}O_4]^+$, calc. 290.1882); EI-MS: m/z 290.0 [$M^+$](60.9), 262.1 (100.0), 248 (21.2), 148.0 (69.0), 133.0 (71.0), 99.0 (21.7); $^1$H-NMR ($CDCl_3$, 300 MHz); $^{13}$C-NMR ($CDCl_3$, 125 MHz).

6β,17β-Dihydroxy-19-nor-4-androsten-3-one (6): White solid; log ε=3.34; $[α]_D^{25}$=126.2 (c 0.012, MeOH); IR ($CHCl_3$); $υ_{max}$ 3389.2 (O—H stretching), 1666 (C=O stretching); HREI-MS m/z 290.1897 ($M^+$, $[C_{18}H_{26}O_3]^+$, calc. 290.1882); EI-MS: m/z 290.1 [$M^+$](23.5), 261.1 (15.0), 246.1 (9.3), 213.1 (27.7), 138.1 (52.5); $^1$H-NMR ($CDCl_3$, 300 MHz); $^{13}$C-NMR ($CD_3OD$, 150 MHz).

10β-Hydroxy-19-nor-4-androsten-3,17-dione (7): White solid; log ε=2.8; $[α]_D^{25}$=−68.8 (c 0.006, MeOH); IR ($CHCl_3$); $υ_{max}$ 3413.9 (O—H stretching), 1723 (C=O stretching); HREI-MS m/z 288.1725 ($M^+$, $[C_{18}H_{24}O_3]^+$, calc. 288.1725); EI-MS: m/z 288.1 [$M^+$](7.0), 272 (10.0), 261.1 (18.8), 138.1 (53.0); $^1$H-NMR ($CDCl_3$, 300 MHz); $^{13}$C-NMR ($CD_3OD$, 100 MHz).

16β,17β-Dihydroxy-19-nor-4-androsten-3-one (8): White solid; log ε=0.9; $[α]_D^{25}$=34.4 (c 0.012, MeOH); IR ($CHCl_3$); $υ_{max}$ 3395 (O—H stretching), 1660 (C=O stretching); HREI-MS m/z 290.1871 ($M^+$, $[C_{18}H_{26}O_3]^+$, calc. 290.1882); EI-MS: m/z 290.1 [$M^+$]290.1 (6), 272.2 (5), 149.0 (15), 110 (35), 82.9 (70). $^1$H-NMR ($CDCl_3$, 300 MHz); $^{13}$C-NMR ($CDCl_3$, 100 MHz).

Compound 2 was obtained as white solid. The molecular formula ($C_{18}H_{26}O_4$) of compound 2 was assigned on the bases of its HREI-MS which showed $[M]^+$ at m/z 306.1842 (calc. 306.1831). The molecular mass was 32 amu higher than 1 which indicated dihydroxylation. The IR spectrum showed characteristic absorption at 3419 cm-1 (hydroxyl) and 1663 cm-1 (ketonic carbonyl). 1H-NMR spectrum showed the presence of a downfield methine proton at δ 3.45 (dd, $J_{aa}$=10.5 Hz, $J_{ae}$=5.7 Hz). The $^{13}$C-NMR spectrum showed two additional downfield carbon signals at δ 70.6 and 79.8, which supported the dihyroxylation. The HMBC correlations of H-4 (δ 5.72 s), $H_2$-6 (δ 2.20 m, 1.52 m) and $H_2$-2 (δ 2.66 m, 2.32 m) with C-10 (δ 70.6) suggested the position of one of the two hydroxyl groups at C-10.

Similarly, the position of second hydroxyl group was assigned at C-12 by the HMBC correlations of $H_2$-11 (δ 1.64, 1.73), H-17 (δ 3.81) and $H_3$-18 (δ 0.84) with C-12 (δ 79.8) The OH at C-10 was assigned β (axial) stereochemistry on the basis of NOE correlation of H-11 (δ 1.64 axial) with OH (δ 5.01) at C-10, and NOESY correlation with H-18 (δ 0.84). The methine proton attached to C-12 (δ 3.45) was a oriented as it showed NOESY correlations with H-9, H-14 and H-17. The metabolite 2 was deduced as 10β,12β,17β-trihydroxy-19-nor-4-androsten-3-one.

The molecular composition of compound 3 ($C_{18}H_{26}O_4$) was determined with HREI-MS where it showed the molecular ion peak $[M]^+$ at m/z 306.1840 (calc. 306.1831). The molecular mass of the observed compound was 32 amu higher than substrate 1. The IR spectrum showed characteristic absorption at 3352 (O—H) and 1664 cm$^{-1}$ (C=O). An additional methine proton at δ 4.02 (q, $J_{ee}$=12.5 Hz, $J_{ea}$=7.5 Hz) was observed in $^1$H-NMR spectrum. The presences of two additional OH groups in compound 3 were supported by the $^{13}$C-NMR spectrum where a new methine and a quaternary carbons were resonated at (δ 70.8) and (δ 70.9) respectively. The COSY-DFQF spectrum showed the coupling between the new methine proton (δ 4.02) and H-17 methine proton (δ 3.30 d, $J_{ae}$=7.44 Hz). The HMBC spectrum showed correlations of H-2 (δ 2.58, 2.27) and H-4 (δ 5.72) with C-10 (δ 70.9), indicating one hydroxylation at C-10. Similarly, H-15 (δ 2.18) showed the HMBC correlations with new methine carbon (δ 70.8). Therefore second hydroxylation was occurred at C-16. The OH (δ 4.59) at C-10 was assigned β stereochemistry on the basis of its NOE correlation with H-8 (δ 1.87) (DMSO-$d_6$). The β stereochemistry of H-16 was assigned through NOESY correlations of methine H-16 (δ 4.02) with $H_3$-18 (δ 0.88). The compound 3 was identified as 10β,16α,17β-trihydroxy-19-nor-4-androsten-3-one.

The HREI-MS of compound 4 showed molecular ion peak $[M]^+$ at m/z 306.1819 ($C_{18}H_{26}O_4$, calc. 306.1831), indicating the presence of two additional OH. The IR absorbances were observed at 3392 (OH) and 1669 cm$^{-1}$ (C=O). The $^1$H-NMR spectrum showed an additional broad singlet of methine proton at δ 4.39 ($W_{1/2}$=1.2 Hz). Two new downfield signals were resonated at δ 73.8 (C-6) and 72.3 (C-10) in $^{13}$C-NMR spectrum which further supported the dihydroxylation in compound 4. The methine proton at δ 4.39 showed HMBC correlations with C-4 (δ 126.2), C-5 (δ 162.4) and C-7 (δ 39.4), indicated second OH at C-6. The $H_2$-1 (δ 2.64, 1.26), $H_2$-2 (δ 2.18, 1.87) and H-4 (δ 5.81) showed HMBC correlations with C-10 (δ 72.3), hence second hydroxylation was inferred at C-10. The methine proton at δ 4.39 showed NOESY correlations with H-4 (δ 5.81) and $H_2$-7 (δ 2.01, 1.26). Therefore, β-OH was placed at C-6. The NOESY correlation of OH (δ 5.01) (DMSO-$d_6$) with C-6 OH (δ 4.49) indicated a β-OH at C-10. Thus the compound 4 was identified as 6β,10β,17β-trihydroxy-19-nor-4-androsten-3-one.

The structures of four known compounds 5-8 were characterized by comparison of their literature reported data with the observed data. The molecular mass of compounds 5, 6 and 8 were 16 amu greater than 1 which showed mono-hydroxylation. Compounds 5, 6 and 8 showed EI-MS [M]$^+$ m/z at 290 whereas compound 7 at m/z 288. Metabolites 5-8 were identified as 10β,17β-dihydroxy-19-nor-4-androsten-3-one (5), 6β,17β-dihydroxy-19-nor-4-androsten-3-one (6), 10β-hydroxy-19-nor-4-androsten-3,17-dione (7) and 16β,17β-dihydroxy-19-nor-4-androsten-3-one (8). Compounds 5 and 6 were previously synthesized by the biotransformation of 1 with *Aspergillus wentii* MRC 200316, whereas compound 7 was synthesized from androstene-3,17,19-trione by aromatase cytochrome P-450 mediated transformation. Metabolite 8 was synthesized from 1 through fermentation with molds.

Anti-leishmanial Assay:

*Leishmania major* was obtained from DESTO laboratories, Pakistan. Blood agar basic medium from BD Company (France) was used in assay, RPMI-1640 medium was purchase from Sigma Aldrich (USA) and fetal bovine serum was obtained from PAA laboratories (UK). 96 well plates used in assay were purchase from COSTER (Italy) and the Neubauer chamber was purchase from Marine field Germany

*Leishmania major* were grown in modified NNN biphasic medium (RPMI-1640+Fetal bovine serum+blood agar in blood) by using normal physiological saline. RPMI 1640 medium was used for culturing of *Leishmania* promastigotes using 10% heat inactivated fetal bovine serum (FBS) as supplemented. Parasites were centrifuged (at log phase) at 2000 rpm for 10 minutes, and washed three times with saline at same speed and time. Fresh culture medium was used for dilution of parasites to acquire a final density of 10$^6$ cells/mL. A 180 μL of medium was added in wells of first row and 100 μL of medium was added in remaining wells of a 96-well microtiter plate. A 20 μL aliquot of the experimental compound was added in medium and serially diluted. A 100 μL aliquot of parasite culture was added in all wells, and two rows were left for negative and positive controls. Negative controls contained only medium, while the positive control received the varying concentrations of standard leishmanicidal compound amphotericin or pentamidine. This plate was than incubated at 21-22° C. for 72 h. The culture was examined microscopically on an improved Neubauer counting chamber. The $IC_{50}$ values of test compounds were calculated by Software Ezfit 5.03 Perella Scientific (USA). All assays were repeated thrice.

Nandrolone (1) and its derivatives, 10β,12β,17β-trihydroxy-19-nor-4-androsten-3-one (2), 10β,16α,17β-trihydroxy-19-nor-4-androsten-3-one (3), 6β,10β,17β-trihydroxy-19-nor-4-androsten-3-one (4), along with four known metabolites, 10β, 17β-dihydroxy-19-nor-4-androsten-3-one (5), 6β,17β-dihydroxy-19-nor-4-androsten-3-one (6) 10β-hydroxy-19-nor-4-androsten-3,17-dione (7) and 16β,17β-dihydroxy-19-nor-4-androsten-3-one (8) were subjected to leishmanicidal assay. The compounds 1-8 showed varying ranges of $IC_{50}$ values, i.e. 29.55 to 80.23 μM against leishmaniasis. Compound 8 showed significant leishmanicidal activity with an $IC_{50}$ value of 29.55 μM as compared to the standard pentamidine $IC_{50}$ 5.09±0.09 μM and it was the most active compound of this series. Compound 3, 4 and 6 showed very low activity, having $IC_{50}$ values of 77.39, 70.90 and 80.23 μM, respectively. Compound 5 and 7 showed moderate leishmanicidal activity with $IC_{50}$ values of 54.94 and 61.12 μM, respectively. The metabolite 8 was found to be more active against *Leishmania* as compared to nandrolone (1) and all other transformed metabolites. Since the only difference between compounds 1 to 8 is the position and number of oxygen atoms, it is suggested that the carbon-oxygen bonding plays an important role in leishmanicidal activity.

Nandrolone (1) has one ketonic carbonyl group at position C-3 and a hydroxyl group at position C-17. It showed significant activity with $IC_{50}$ 32.0 μM. Compound 2 was found to be inactive against the leishmaniasis with an $IC_{50}$ greater than 100 μM. Compound 2 has two hydroxyl groups, one at C-10 and second at C-12, along with ketonic carbonyl at C-3, both have 13 stereochemistry. Compound 3 also has two more hydroxyl groups as compared to nandrolone (1) and it was very low activity with an $IC_{50}$ of 77.39 μM. Compound 4 also showed very low activity with an $IC_{50}$ of 70.90 μM. It was also dihydroxylated having hydroxyl groups at C-6 and C-10, both having β orientated hydroxyl groups. The position of the hydroxyl group has a significant effect on activity. Monohydroxylated compound 5 showed low activity having activity $IC_{50}$ of 54.94 μM. In this compound, hydroxylation occurs at C-10. On the other hand when hydroxylation occurs at C-6, activity again decreases. This was observed in case of compound 6. Compound 7 has a ketonic carbonyl group instead of a hydroxyl group at C-17, and also showed a very low activity against leishmaniasis, with an $IC_{50}$ of 80.23 μM. Compound 8 showed significant activity against leishmaniasis. Compound 8 is mono hydroxylated having β hydroxylation at C-16. The $IC_{50}$ was 29.55 M, which is comparable to compound 1. Compounds 1 and 8 were considered as having significant activity when compared to the standards, i.e. pentamidine ($IC_{50}$=5.09+0.09 M) and amphotericin B ($IC_{50}$=0.29±0.05 μM).

TABLE 1

Results of leishmanicidal activity of nandrolone (1) and its derivatives (2-8).

| Compound No. | Name | Leishmanicidal Activity ($IC_{50}$ in μM) |
|---|---|---|
| 1 | Nandrolone-17β-Hydroxy-19-nor-4-androsten-3-one | 32.0 ± 0.5 |
| 2 | 10β,12β,17β-Trihydroxy-19-nor-4-androsten-3-one | >100 |
| 3 | 10β,16α,17β-Trihydroxy-19-nor-4-androsten-3-one | 77.39 ± 5.52 |
| 4 | 6β,10β,17β-Trihydroxy-19-nor-4-androsten-3-one | 70.90 ± 1.16 |
| 5 | 10β,17β-Dihydroxy-19-nor-4-androsten-3-one | 54.94 ± 1.01 |
| 6 | 6β,17β-Dihydroxy-19-nor-4-androsten-3-one | 80.23 ± 3.39 |
| 7 | 10β-Hydroxy-19-nor-4-androsten-3,17-dione | 61.12 ± 1.39 |
| 8 | 16β,17β-Dihydroxy-19-nor-4-androsten-3-one | 29.55 ± 1.14 |
| Standard | Pentamidine | 5.09 ± 0.09 |
|  | Amphotericin B | 0.29 ± 0.05 |

TABLE 2

¹H-NMR (300 MHz) Chemical Shift Assignments (δ in ppm, J in Hz) of compounds 1-4.

| Position | 1 | 2 | 3 | 4 |
|---|---|---|---|---|
| 1 | 1.78 m, 1.47 m | 2.19 m, 1.92 m | 1.86 m, 1.03 m | 2.64 m, 2.27 m |
| 2 | 1.87 m, 1.10 m | 2.66 m, 2.32 m | 2.58 m, 2.27 m | 1.87 m, 2.16 m |
| 3 | — | — | — | — |
| 4 | 5.57 m | 5.72 s | 5.72 s | 5.81 s |
| 5 | — | — | — | — |
| 6 | 2.49 m, 2.33 m | 2.21 m, 1.52 m | 2.81 m, 2.32 m | 4.38 m |
| 7 | 1.87 m, 1.03 m | 2.60 m, 1.28 m | 2.19 m, 1.87 m | 2.0 m, 1.25 m |
| 8 | 1.41 m | 1.80 m | 1.87 m | 1.50 m |
| 9 | 1.01 m | 1.15 m | 1.07 m | 1.08 m |
| 10 | 2.21 m | — | — | — |
| 11 | 1.53 m, 2.30 m | 1.73 m, 1.64 m | 1.73, 1.67 m | 1.73 m, 1.63 m |
| 12 | 2.32 m, 2.25 m | 3.45 dd, J = 10.5, 5.7 | 1.87 m, 1.12 m | 1.50 m, 1.20 m |
| 13 | — | — | — | — |
| 14 | 0.85 td, J = 11.6, 4.0 | 0.96 m | 0.85 m | 1.06 m |
| 15 | 1.62 m, 1.32 m | 1.63 m, 1.40 m | 2.18 m, 1,27 m | 1.63 m, 1.36 m |
| 16 | 1.98 m, 1.47 m | 2.20 m, 1.52 m | 4.02 q, J = 12.48, 7.5 | 2.16 m, 2.07 m |
| 17 | 3.49 t, J = 8.8 | 3.81 t, J = 8.1 | 3.30 d, J = 7.44 | 3.50 t, J = 8.4 |
| 18 | 0.81 s | 0.84 s | 0.88 s | 0.82 s |

TABLE 3

¹³C-NMR Chemical Shift Assignments of (δ in ppm) compounds 1-4.

| Position | 1[a] | 2[b] | 3[c] | 4[b] |
|---|---|---|---|---|
| 1 | 27.2 | 34.6 | 32.8 | 34.7 |
| 2 | 37.7 | 33.1 | 34.5 | 34.2 |
| 3 | 202.9 | 202.2 | 202.3 | 202.7 |
| 4 | 124.7 | 124.9 | 124.8 | 126.1 |
| 5 | 170.8 | 168.0 | 168.5 | 162.4 |
| 6 | 36.5 | 31.9 | 33.1 | 73.7 |
| 7 | 31.9 | 34.4 | 34.5 | 39.4 |
| 8 | 41.6 | 35.5 | 35.9 | 30.6 |
| 9 | 51.0 | 53.3 | 54.6 | 54.5 |
| 10 | 43.8 | 70.6 | 70.9 | 72.3 |
| 11 | 27.7 | 29.9 | 20.9 | 20.9 |
| 12 | 37.2 | 79.8 | 38.2 | 37.7 |
| 13 | 44.1 | 49.5 | 43.5 | 44.2 |
| 14 | 51.2 | 49.8 | 47.9 | 51.1 |
| 15 | 24.1 | 24.0 | 36.0 | 24.2 |
| 16 | 30.6 | 30.8 | 70.8 | 30.6 |
| 17 | 82.3 | 82.5 | 81.9 | 82.3 |
| 18 | 11.6 | 6.5 | 12.4 | 11.5 |

[a] = 75 MHz
[b] = 125 MHz
[c] = 150 MHz

The invention claimed is:

1. A method for the treatment of leishmaniasis with nandrolone [17β-hydroxy-19-nor-4-androsten-3-one] or a derivative thereof consisting of administering an effective amount to a patient in need thereof.

* * * * *